United States Patent
Rakshit et al.

(10) Patent No.: US 11,099,571 B2
(45) Date of Patent: Aug. 24, 2021

(54) AUTONOMOUS VEHICLE TAKEOVER BASED ON RESTRICTED AREAS

(71) Applicant: INTERNATIONAL BUSINESS MACHINES CORPORATION, Armonk, NY (US)

(72) Inventors: Sarbajit K. Rakshit, Kolkata (IN); James E. Bostick, Cedar Park, TX (US); John M. Ganci, Jr., Raleigh, NC (US); Martin G. Keen, Cary, NC (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 98 days.

(21) Appl. No.: 16/190,512

(22) Filed: Nov. 14, 2018

(65) Prior Publication Data

US 2020/0150667 A1 May 14, 2020

(51) Int. Cl.
| | | |
|---|---|---|
| *G05D 1/02* | (2020.01) | |
| *G01C 21/34* | (2006.01) | |
| *G05D 1/00* | (2006.01) | |
| *A61B 5/18* | (2006.01) | |
| *B60C 9/00* | (2006.01) | |

(52) U.S. Cl.
CPC ............ *G05D 1/0214* (2013.01); *A61B 5/18* (2013.01); *B60C 9/00* (2013.01); *G01C 21/3461* (2013.01); *G05D 1/0061* (2013.01); *G05D 1/0223* (2013.01); *G05D 2201/0213* (2013.01)

(58) Field of Classification Search
CPC ..... B60W 60/0051; B60W 2050/0071; B60W 30/12; G05D 1/0061; G05D 1/0088; G05D 1/0214; G06K 9/00791; G06K 9/00798; G01C 21/3461
See application file for complete search history.

(56) References Cited

U.S. PATENT DOCUMENTS

| | | |
|---|---|---|
| 8,874,301 B1 | 10/2014 | Rao et al. |
| 9,981,669 B2 | 5/2018 | Gordon et al. |
| 9,988,055 B1 | 6/2018 | O'Flaherty et al. |
| 10,593,202 B1 * | 3/2020 | Christensen ......... G08B 25/006 |

(Continued)

OTHER PUBLICATIONS

"Lane Departure Warning System", Wikipedia, page last edited on Jul. 9, 2018. Retrieved on Oct. 15, 2018 from the Internet URL: <https://en.wikipedia.org/wiki/Lane_departure_warning_system>, 13 pgs.

(Continued)

*Primary Examiner* — Kenneth J Malkowski
(74) *Attorney, Agent, or Firm* — Daniel Yeates; Matthew M. Hulihan; Heslin Rothenberg Farley & Mesiti PC (57) ABSTRACT

Autonomous vehicle takeover based on restricted areas includes receiving position data of a vehicle, the position data indicating a position of a vehicle traveling in an area, correlating the received position data to a map including mapped areas designated as non-roadway areas, where the correlating determines that the vehicle is traveling in a designated non-roadway area, checking one or more restrictions placed on vehicular travel in the non-roadway area in which the vehicle is traveling and, based on the one or more restrictions, performing processing to undertake action(s), the action(s) including controlling function(s) of the vehicle.

18 Claims, 5 Drawing Sheets

(56) References Cited

U.S. PATENT DOCUMENTS

| | | | |
|---|---|---|---|
| 2007/0152804 A1* | 7/2007 | Breed | B60W 30/16 |
| | | | 340/435 |
| 2015/0175159 A1* | 6/2015 | Gussner | B60W 30/08 |
| | | | 701/1 |
| 2017/0106876 A1* | 4/2017 | Gordon | B60W 30/182 |
| 2017/0153636 A1 | 6/2017 | Boesen | |
| 2019/0056738 A1* | 2/2019 | Prasad | G08G 1/161 |

OTHER PUBLICATIONS

"Driver Drowsiness Detection", Wikipedia, page last edited on Aug. 17, 2018. Retrieved on Oct. 15, 2018 from the Internet URL: <https://en.wikipedia.org/wiki/Driver_drowsiness_detection, 4 pgs.
Mell, Peter, et al., "The NIST Definition of Cloud Computing", NIST Special Publication 800-145, Sep. 2011, Gaithersburg, MD, 7 pgs.

* cited by examiner

AUTONOMOUS VEHICLE TAKEOVER BASED ON RESTRICTED AREAS

BACKGROUND

Advances continue to be made in the amount of self-control given to vehicles. Fully autonomous vehicles (sometimes referred to as driverless, self-driving, or robotic cars) may be able to drive from point A to point B unassisted by a human operator, though it is not necessarily the case that a fully autonomous vehicle always operates in a driverless manner. Many vehicles are 'semi-autonomous' in that they exert some level of autonomy in performing targeted function(s), such as self-parking or adaptive cruise control functions. It is anticipated that a mixture of fully autonomous, semi-autonomous, and traditional human-operated vehicles will occupy the roads for years.

SUMMARY

Shortcomings of the prior art are overcome and additional advantages are provided through the provision of a computer-implemented method. The method receives position data of a vehicle. The position data indicates a position of a vehicle traveling in an area. The method correlates the received position data to a map including mapped areas designated as non-roadway areas. The correlating determines that the vehicle is traveling in a designated non-roadway area. The method checks restriction(s) placed on vehicular travel in that non-roadway area in which the vehicle is traveling. Based on the restriction(s), the method performs processing to undertake action(s), including controlling function(s) of the vehicle.

Further, a computer system is provided that includes a memory and a processor in communication with the memory, wherein the computer system is configured to perform a method. The method receives position data of a vehicle. The position data indicates a position of a vehicle traveling in an area. The method correlates the received position data to a map including mapped areas designated as non-roadway areas. The correlating determines that the vehicle is traveling in a designated non-roadway area. The method checks restriction(s) placed on vehicular travel in that non-roadway area in which the vehicle is traveling. Based on the restriction(s), the method performs processing to undertake action(s), including controlling function(s) of the vehicle.

Yet further, a computer program product including a computer readable storage medium readable by a processing circuit and storing instructions for execution by the processing circuit is provided for performing a method. The method receives position data of a vehicle. The position data indicates a position of a vehicle traveling in an area. The method correlates the received position data to a map including mapped areas designated as non-roadway areas. The correlating determines that the vehicle is traveling in a designated non-roadway area. The method checks restriction(s) placed on vehicular travel in that non-roadway area in which the vehicle is traveling. Based on the restriction(s), the method performs processing to undertake action(s), including controlling function(s) of the vehicle.

Additional features and advantages are realized through the concepts described herein.

BRIEF DESCRIPTION OF THE DRAWINGS

Aspects described herein are particularly pointed out and distinctly claimed as examples in the claims at the conclusion of the specification. The foregoing and other objects, features, and advantages of the invention are apparent from the following detailed description taken in conjunction with the accompanying drawings in which:

DETAILED DESCRIPTION

Described herein are approaches for autonomous vehicle takeover based on restricted areas. An autonomous vehicle is one that has some capabilities to function, for instance drive or perform other functions of the vehicle, with little or no human input. Autonomous vehicles include fully-autonomous vehicles—referring primarily to those that can navigate unassisted from one point to another, taking into consideration other traffic, traffic signals, the like—and semi-autonomous vehicles. Examples are described and depicted in the context of cars as the subject vehicles, but principles presented herein apply to other types of vehicles, such as other motorized vehicles including trucks, busses, motorcycles, recreational vehicles (RVs), all-terrain vehicles, snowmobiles, or any other motorized transportation device.

Aspects described herein present approaches for an autonomous vehicle to automatically takeover, e.g. from a human operator of the vehicle, control of at least some vehicle function(s) based on restrictions placed on vehicular travel in non-roadway areas. Example functions include, but are not limited to, automatically governing speed of the vehicle to slow/stop the vehicle, and guiding the vehicle onto a nearby roadway.

Mapped areas can be designated as being restricted. Such areas include non-roadway areas and/or any other areas marked as restricted and not suitable for vehicular traffic at given time(s). This can enable location-aware detection of possible risks to the safety of people and other objects in the area. If a vehicle is traveling in a non-roadway area, for instance a public park, a sidewalk, or a pedestrian area, restrictions on vehicular travel can be identified and serve as a basis for automatically and authoritatively undertaking actions to control function(s) of the vehicle, and thereby rectify a potentially dangerous situation and/or mitigate damage to objects in the area.

In a particular example, a process receives position data of a vehicle, which indicates a position of the vehicle traveling in an area. Example position data is Global Positioning Satellite (GPS) position data. The received position data is then correlated to map(s) that include mapped areas designated as being restricted, i.e. having restriction(s) placed thereon. Example restricted areas include non-roadway areas—areas that are not roadway(s) where vehicles could, should, or are intended to travel. Restricted areas could be roadways that are temporarily closed, cordoned off, or otherwise restricted from use, for instance to serve as a parade route or for a road-race, as examples.

The process can correlate the position data to a map and determine/identify that the vehicle is traveling in, e.g., a non-roadway (or other restricted) area. Such travel in a non-roadway area may pose a potential danger posed to people and objects in the non-roadway area. Thus, restrictions can be placed on vehicular travel in these areas. The process can check the restriction(s) placed on the particular area in which the vehicle travels. Based on the restriction(s), processing can be performed by computer system(s) to undertake action(s), including action(s) that control function(s) of the vehicle. An example such function is to automatically govern the vehicle's speed, for instance to slow the vehicle to a stop or limit it to a maximum speed, for instance 5 miles per hour. In this case, a restriction can include a maximum speed of travel for given vehicle(s) in the non-roadway area. Additionally or alternatively, certain thresholds can be set to invoke actions. An example threshold is a speed that, when exceeded by a vehicle traveling in a restricted area, invokes a call or other notification to police or another entity, and may automatically invoke functions of the vehicle.

Autonomous capabilities of the vehicle may enable a control system, such as a remote computer system with authoritative control over autonomous capabilities of the vehicle, to control the vehicle to perform functions described herein, such as pulling-over or driving to a selected area. Thus, based on the map, a process can locate a safe area to which the vehicle is to be driven, for instance a nearby location that the control system locates on the map, and use the vehicle's GPS to guide the vehicle to that location. A fully autonomous vehicle may be able to drive the vehicle user home or to an emergency center.

Sometimes travel of a vehicle in a non-roadway area is a result of the driver's physical state. Aspects can also provide safer passage to a given vehicle and surrounding vehicles in situations when a driver's physical state presents a danger, for instance when the driver has fallen asleep or experiences a medical emergency. This can trigger action(s) by the vehicle and takeover of functions of the vehicle.

Not all vehicles have full autonomous capability and/or have been fully tested in terms of their autonomous capabilities, thus full autonomous control may not be possible or may not be verified as being safe. Even in these cases, certain other actions can be quickly accomplished, for instance to activate vehicle lights/flashers, sound the horn, or send alerts to surrounding vehicles and/or automated communications to emergency services, as examples. Self-governing engines may enable automatically slowing the vehicle down to a stop. As noted, some capabilities may enable finding a nearby safe place to stop the vehicle.

In some examples, fully autonomous vehicles may be able to determine and distinguish between physical conditions of the driver, for instance that the driver has fallen asleep or that the driver is experiencing a more serious medical issue, and drive the person to an appropriate location, for instance home in the case that the driver has fallen asleep or to an emergency room in the case that the driver is experiencing a medical emergency.

Example issues that could be sensed and reacted-to could include one or more of the following:
  Position data indicates that the vehicle is traveling in a designated non-roadway area;
  Biometric information sent from a smart watch or other device (for example a heart monitor, pace-maker, or pulse detector) and/or other health indicators (information about the driver indicating that the driver has, for instance, a pace maker) shows a user has lost a pulse;
  Image analysis identifies other health issues, such as drowsiness, drunkenness, sweating, vomiting, etc.;
  The driver has fallen asleep, whether detected biometrically or with image analysis;
  The vehicle determines that it is traveling on the wrong side of the road, or on a sidewalk or grassy area, as examples;
  Smartwatch/sensor(s) track blood sugar changes and alerts the driver to pull over and take remedial actions;
  Sensor(s) detect dehydration levels to monitor driver physical state.

Processing by control system(s) can take actions in these and other situations to control functions of the vehicle, for instance to govern the vehicle speed and/or guide it in a safer direction, in order to prevent or mitigate damage to people or property.

Figure 1:
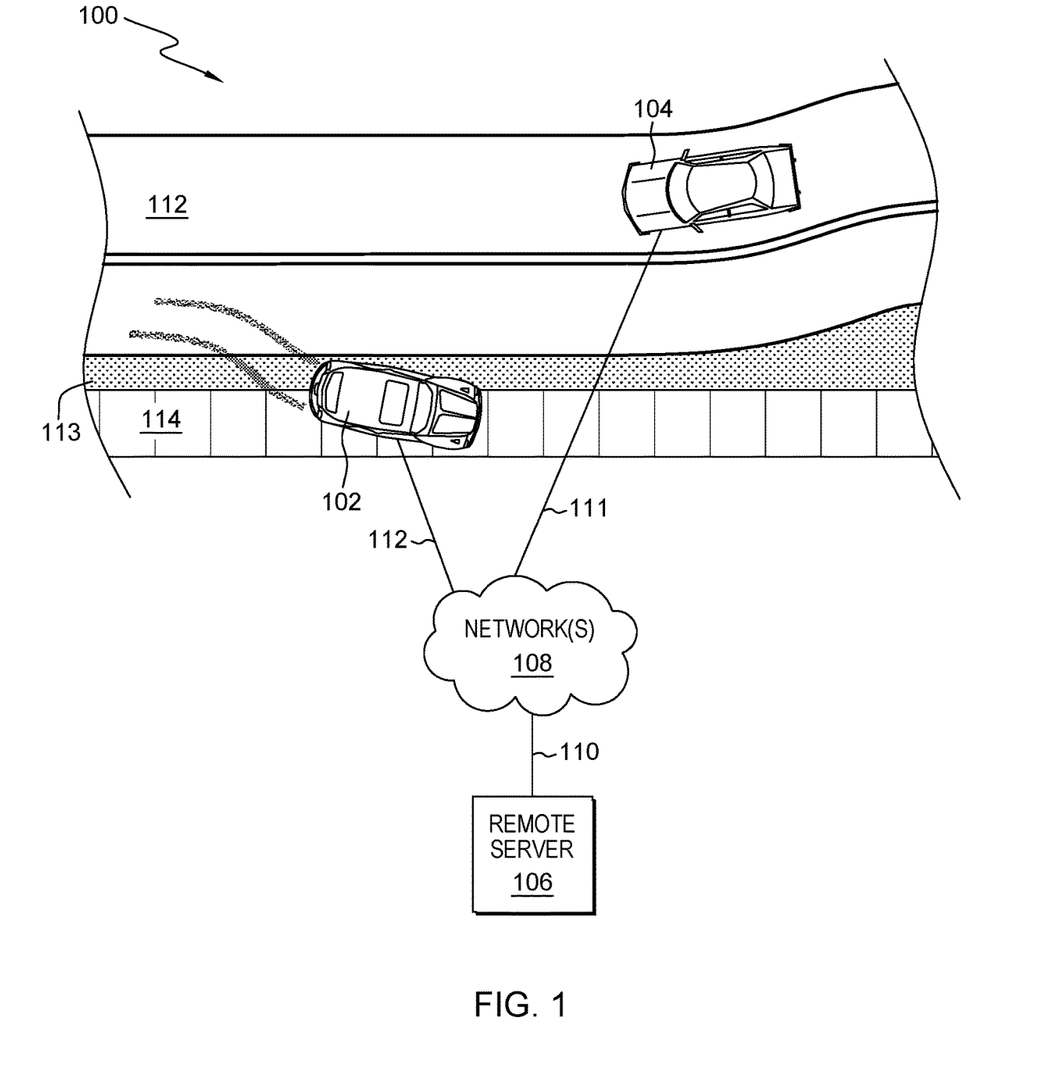
FIG. 1 depicts an example environment to incorporate and use aspects described herein.

FIG. 1 depicts an example environment 100 to incorporate and use aspects described herein. The environment includes roadway 112, which is a two-lane, two-way road. Sidewalk 114 is proximate roadway 112, with grass buffer 113 therebetween. Vehicles 102, 104 travel on roadway 112. Environment 100 also includes a remote server 106 coupled to, and in communication with, network(s) 108 via communications link 110. Vehicles 102 and 104 are in communication with network 108 via communications links 112 and 111, respectively, and communicate with remote server 106.

In some examples, each vehicle 102, 104 includes or is associated with a respective computer system that is connected to network(s) 108 via a wireless communication link, such as a cellular, Wi-Fi, or other type of wireless connection. More generally, communications links 111 and 112 may be or include any appropriate wireless or wired communication link for communicating data. In some embodiments, connectivity of each vehicle to network(s) 108 can be made by-proxy via a user's mobile device. For instance, a mobile device, such as a smartphone, of an occupant of the vehicle is connected to network 108(s) via a cellular or Wi-Fi connection, as examples. Additionally, as noted, the vehicles can also be in communication with remote server 106 via network(s) 108 and/or another network.

In some aspects, a vehicle (or computer system associated therewith, such as a smartphone of an occupant) sends information about the vehicle and occupants to remote server 106 via network(s) 108 and across the communications link(s). Vehicle information can include any appropriate information about the vehicle, for instance information that is or might be useful to remote server 106 in performing aspects described herein. Such information includes, as examples, information about vehicle capabilities, including any autonomous capabilities, dimensions (e.g. dimensions of the vehicle, footprint, shape, etc., as examples examples), make and model of the vehicle, driving direction and other data about vehicle travel, and position data. Occupant information can include any information about occupants of the vehicle, for instance biometric or other information gathered by mobile devices or other computer systems. In some examples, mobile devices of vehicle occupants send occupant information about occupants to remote server 106 directly through a separate connection they have to network(s) 108, or alternatively by sending to an onboard computer system of the vehicle for it to pass to remote server 106 along with vehicle information.

Either or both of vehicles 102, 104 are autonomous vehicles (fully or semi-autonomous) and controllable via one or more computer systems. In some examples, a vehicle may be automatically repositioned, in which movement and/or repositioning of the vehicle may be automated and performed and/or coordinated by computer system(s). In some embodiments, the remote server 106 and/or a computer system acting on behalf of, or in response to commands from, remote server 106, such as an on-board computer system of the vehicle, can control such an autonomous vehicle to takeover control of function(s), such as to drive the vehicle or control status or operating states of various components thereof, as examples.

In the example of FIG. 1, vehicle 102 has exited roadway 112 and traveled over grass 113 onto sidewalk 114. This presents a potentially serious safety hazard to objects and people, for instance the driver and any individuals on sidewalk 114. Aspects described herein can provide location-aware detection of scenarios like this and initiate appropriate action(s). In one aspect, a vehicle (e.g. a computer system thereon) may be configured to understand GPS position and make correlations to existing maps, for positive identification that the vehicle is in a place of danger, such as a designated non-roadway or other restricted area. Based on this assessment, a control system, such as an onboard computer system of the vehicle and/or a remote system, can perform processing to undertake action(s), for instance control of function(s) of the vehicle. This can include taking control over the speed and steering of the vehicle, for instance to slow the vehicle down to a stop while guiding the vehicle back toward the roadway. Other actions can be initiated, for instance a call to emergency services.

Biometrics and other methods can be leveraged to determine a physical state (heart attack, passed out, etc.) of a driver of a vehicle if the driver has lost control. Various actions can be taken depending on the severity of the issue discovered. In a particular example, a vehicle takeover system automatically takes control of the vehicle such that the vehicle becomes self-driving.

In situations where a given vehicle is not fully autonomous, actions to take can make use of one or more autonomous capabilities that the vehicle does possess. Even though a vehicle may not be capable of self-driving, there may be at least some points of control over function(s) of the vehicle, for instance control over the engine to govern top speed, control over braking, activation of lights, directional indicators, flashers, horn, control to change a current gear to neutral, and so on. This can be used to alert surrounding vehicles (e.g. vehicle 104 in FIG. 1) of a potentially dangerous situation.

Additionally or alternatively, a vehicle possessing the capability could automatically send electronic communication(s) to devices such as those within a threshold distance of the vehicle. Such devices could be computer system(s) of nearby vehicles or occupants thereof. A standard vehicle-to-vehicle communications mechanism could be established allowing messages to be exchanged for warning or general information purposes. In the receiving vehicles, visual and/or audio alert(s) could be raised to occupants thereof. In the example of FIG. 1, vehicle 104 could be warned that vehicle 102 has exited the roadway 112. Vehicle 104 could use this as a trigger, either automatically, if fully autonomous, or manually, based on human operation, to proceed with caution.

In some specific examples, a capable vehicle could look for a closest location to where it would be safe to pull-over. A fully autonomous vehicle may be able to take the user home or to an emergency medical facility if a medical emergency is recognized. A less capable or unverified (in terms of its ability for safe self-driving) vehicle may be controlled to pull-over at a nearest location not designated as non-roadway and call emergency services automatically, for instance.

Cognitive computing could be leveraged to connect cars and acquire data from sensors and systems, to both improve the in-car experience and enhance safety of vehicles, roadways, and restricted areas.

Various mechanisms can be leveraged to support activities presented herein. Vehicle and occupant detection systems/capabilities can identify physical states of occupants, for instance detect when a driver is falling asleep. The recognition of various physical states can serve as triggering events to trigger devices to perform processing to undertake actions. Cameras and image analysis can also be leveraged to help identify driver physical state. Biometrics could be leveraged to determine whether the driver is experiencing health or medical issues.

GPS-enabled devices, such as the onboard computer system and/or occupant mobile devices, can find an exact, current location of the vehicle. Associated mapping software could understand the location and pinpoint that location to a specific area and/or roadway as indicated by map data. This can be used to not only correlate to areas on maps, but also identify a safe spot or other desired locations to pull-over, for instance the driver's home or a medical facility such as a hospital.

On a user (i.e. vehicle driver) level, known issues can be tracked through a knowledge-base. The knowledge-base can be configured by a user and/or may be fed information by systems having information about the user. For example, medical records could be fed to the system if so configured. This information can be used to help ascertain possible physical states of the driver, including whether the driver may be experiencing any health-related issues, and, if so, what those specific issue(s) are.

From a vehicle standpoint, autonomous capabilities for involved vehicles could be known by the system. 'System' here could refer to a remote server or collection of computer systems, as an examples. A standard communication protocol for vehicle communication to the system could be put into place so that known capabilities of the vehicle can be taken advantage of during emergencies. For instance, vehicle metadata, such as parameters, capabilities, dimensions, etc. can be maintained by each vehicle and shared with a remote (e.g. cloud) server. Answers to the following questions could be sent from the vehicle to a backend system, e.g. in XML format, to be read by software performing processing in accordance with aspects described herein, and information addressing these could be stored in the knowledge-base as well:

Can the vehicle run in a fully autonomous fashion?
Can steering be controlled (e.g. by a computer system)?
Can the vehicle change speeds (speed up and slow down—control the engine) without human intervention (e.g. by computer control)?
Can the vehicle read maps/map data (for instance does it have built-in GPS)?
Can the vehicle detect lane deviation?

Thus, a process can determine autonomous capabilities of the vehicle by receiving from the vehicle information that informs of whether, and to what extent, the vehicle can autonomously drive itself, whether the vehicle possesses automatic steering capability, whether the speed of the vehicle can be controlled by the vehicle without driver intervention, whether the vehicle reads map data, and whether the vehicle possesses lane detection capability, as examples.

When an issue is detected by the system in real-time, for instance that the vehicle is traveling in a designated non-roadway area, restrictions on vehicular travel in that area are checked and identified, and processing can be triggered for performance to undertake desired actions, at least some of which include control over vehicle function(s).

As noted, capabilities of the vehicle can be identified and known as part of a central knowledge-base. This information could be stored in a computer system of the vehicle to enable faster real-time processing and takeover of vehicle functions.

If the vehicle is capable of driving autonomously, the vehicle (i.e. a control system that can control the functions, such as an onboard computer system) could takeover driving control and steer the vehicle to a safe area. Additionally or alternatively, the vehicle could takeover control for a duration of time determined by the system and control the speed of the vehicle to within a roadway speed limit. In some examples, a backend system, such as a remote server dictates the actions/control to take by the onboard computer system.

If the system determines that the user has fallen asleep but has since woken-up, the user might optionally be permitted to take back control based on a defined event, such as selection of a button for restoring driver control. If the system determines that the user is ill, inebriated, or otherwise physically incapable for medical or safety reasons of driving, it may not allow restoration of human control or intervention. The vehicle could therefore remain in a forced-autonomous mode for a remainder of a ride to a destination. The destination could be selected based on any of various factors. In some cases, the vehicle takes the user to a known location, such as the user's home, relying on the vehicle's built in GPS guidance and/or guidance provided by an occupant's mobile device, as examples. In examples where illness might be determined to be severe (e.g. possible heart attack), the system could control the vehicle to drive to a nearest emergency location. In situations where physical activity is illegal, egregious, or particularly dangerous, the system could control the vehicle to drive it to a law enforcement facility or a secure area to contain the vehicle and its occupants.

Controlling a function of the vehicle could include initiating guiding the vehicle back onto a roadway adjacent to the non-roadway area in which the vehicle was determined to be traveling, and may navigate a vehicle slow-down process to slow or stop the vehicle. This may be useful in cases where the vehicle is not capable of fully autonomous driving but has even a rudimentary capability to steer and control speed. In some examples, controlling a function of the vehicle shifts to lower gears to slow the vehicle down, shifts to neutral so that no acceleration is possible, and/or slows the vehicle and, if possible, moves the vehicle to a side of the roadway or other area that decreases risk to the safety of others in the area. In a particular example, actions taken include automatically turning on flashers of the vehicle, activating the horn to blow and alert nearby vehicles, sending a communication from the known GPS location of the vehicle to vehicles within a threshold range of the GPS location to notify them of a possible dangerous situation, and/or if possible, switching to neutral or a lower gear to slow the vehicle down.

Locations can be mapped such that software can understand that a vehicle should not travel through a designated non-roadway area, or should be subject to restrictions if traveling therethrough. 'Designated' in this sense could be an explicit designation, e.g. by an admin or user to mark areas of the map as restricted from vehicular travel. Implicit designations may be recognized based, for instance, on what is recognized as being present on the map (buildings, waterways, public pedestrian areas, grassy areas, etc.), the terrain indicated on the map, presence of nearby roadways, and any other indicators, such as correlations to news or event information that indicates that people will be in a given area at a given time and therefore vehicular travel therein is to be prohibited.

New roads are being developed and map data may lag behind. Given this, aspects described herein might be restricted to apply only to areas known to be designated as non-roadway or other restricted areas. In other words, computer systems performing processes described herein could refrain from taking action to control vehicles travelling in an area unless that area is known to be restricted, in order to avoid false positives.

Thus, areas may be mapped to indicate them as non-roadways, with various levels of restrictions per each area. A public park may have non-roadway areas in which no vehicles except maintenance vehicles should travel. Parking lots are non-roadway areas but obviously vehicular travel is permitted therein. In such a case, a restriction could indicate that vehicles can travel no faster than 5 miles per hour (MPH) when in a parking lot area. Zones could be mapped for speeds not to exceed, e.g. 5 MPH. Functions of vehicles in the area could then be regulated by a control system, for instance to regulate a maximum speed at which those vehicles can travel in that area.

Even in areas where vehicles are not intended to travel, there may be situations where restrictions would permit vehicles, or some subset of vehicles, to be present—either unrestricted or with restrictions placed thereon. There may be a legitimate reason that a vehicle is on a grassy field or sidewalk (for instance to perform a delivery or maintenance, move furniture or equipment, or for a special event, as examples). Alternatively, certain types of emergency vehicles, like police cars, ambulances, or firetrucks, may be excluded from general restrictions against vehicular traffic. In some examples, even exempted vehicles may be subject to restrictions, for instance a cap on their speed. Thus, restrictions placed on an area can indicate an exception for designated privileged vehicles. When such a privileged vehicle is in the area, however, function(s) thereof could still be controlled, for instance to regulate a maximum speed at which the privileged vehicle can travel in the non-roadway area.

A vehicle entering a restricted area may be allowed to proceed as long as it remains in compliance with any restrictions thereon. If one or more restrictions are violated (for instance the vehicle exceeds a maximum speed), then that can trigger aspects described herein, for instance to initiate undertaking of actions to takeover control of vehicle functions.

Additionally, it is noted that restrictions indicated for an area could be temporary. This may be particularly useful when restrictions are placed on roadways that are generally used for vehicular travel but may be restricted from time-to-time for events or other purposes.

Figure 2:
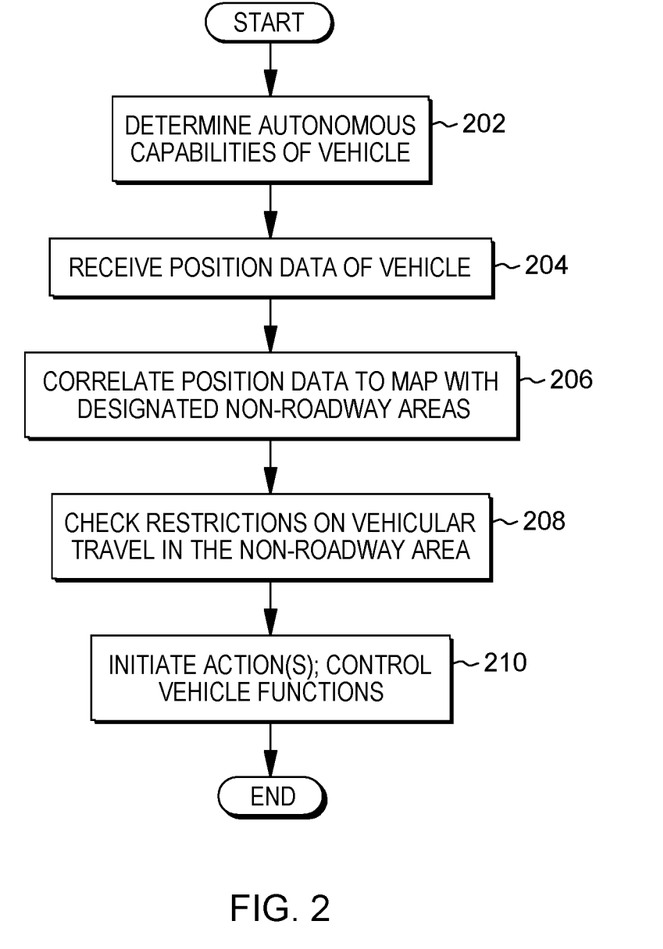
FIG. 2 depicts an example process for autonomous vehicle takeover based on restricted areas, in accordance with aspects described herein.

FIG. 2 depicts an example process for autonomous vehicle takeover based on restricted areas, in accordance with aspects described herein. In some examples, the process is performed by one or more computer systems, such as those described herein, which may include one or more computer systems of a vehicle, an occupant of the vehicle, and/or one or more systems remote from the vehicle, such as a backend or cloud servers, and/or one or more other computer systems. Such systems may be deemed a control system as used herein. In some examples, aspects of the process are performed by one system (such as a remote system) which initiates other aspects for performance by another system to effect actions described herein.

The process begins by determining (202) autonomous capabilities of a vehicle. This can include receiving data, from the vehicle, informing of various functions that may be controllable by computer system(s). Example data can indicate whether, and to what extent, the vehicle can autonomously drive itself; whether the vehicle possesses automatic steering capability; whether speed of the vehicle can be controlled by the vehicle without driver intervention; whether the vehicle reads map data; and whether the vehicle possesses lane detection capability, as examples.

The process proceeds by receiving (204) position data of the vehicle, the position data indicating a position of the vehicle traveling in an area. Position data can be or include GPS data, for example, and indicate coordinates or other location information of the vehicle. The process correlates (206) the received position data to a map. The map includes mapped areas that are designated (explicitly or by implication) as non-roadway areas. The correlating can therefore determine whether the vehicle is traveling in a designated non-roadway area. If the vehicle is not traveling in a designated non-roadway, the process can end (or return to another aspect, such as 204). Otherwise, the process checks (208) restriction(s) placed on vehicular travel in the non-roadway area in which the vehicle is traveling. An example restriction indicates that no vehicular travel is permitted in the area at all. Another example restriction indicates a maximum speed of travel for any vehicle in the non-roadway area. Restrictions can additionally indicate an exception for designated privileged vehicles, such as law enforcement and emergency vehicles. Privileged vehicles may face no restrictions or a different set of restriction(s) than non-privileged vehicles.

Based on the one or more restrictions, the processing is performed (210) to undertake at least one action. The at least one action can include controlling function(s) of the vehicle. An example of controlling a function of the vehicle is to automatically control a speed of the vehicle, to at least slow the vehicle from an initial speed to a slower speed. In some cases, controlling the function include governing a maximum speed of the vehicle while the vehicle is present in the non-roadway area. In cases where the restriction(s) indicate an exception for designated privileged vehicles, controlling a function includes regulating a maximum speed at which the privileged vehicle can travel in the non-roadway area.

Additionally or alternatively, controlling a function includes initiating guiding the vehicle back onto a roadway adjacent to the non-roadway area.

Controlling a function of the vehicle can include automatically activating audio and/or visual alert devices of the vehicle, for instance a horn of the vehicle and flashers or other lights.

An action undertaken can additionally or alternatively include locating, based on the map, a safe area to which the vehicle is to be driven. Controlling the function(s) can include in that example directing autonomous vehicle navigation of the vehicle to drive the vehicle to the safe area.

The action(s) can additionally or alternatively include automatically initiating an alert to law enforcement based on observing that the vehicle travels in the non-roadway in excess of a threshold speed, and/or automatically sending electronic communication(s) from the vehicle to device(s) within a threshold distance of the vehicle.

As an enhancement, the process can ascertain a physical state of the driver. The ascertained physical state could indicate a medical emergency, and the safe area to which the vehicle may be driven automatically can include an emergency health care facility.

Although various examples are provided, variations are possible without departing from a spirit of the claimed aspects.

Figure 3:
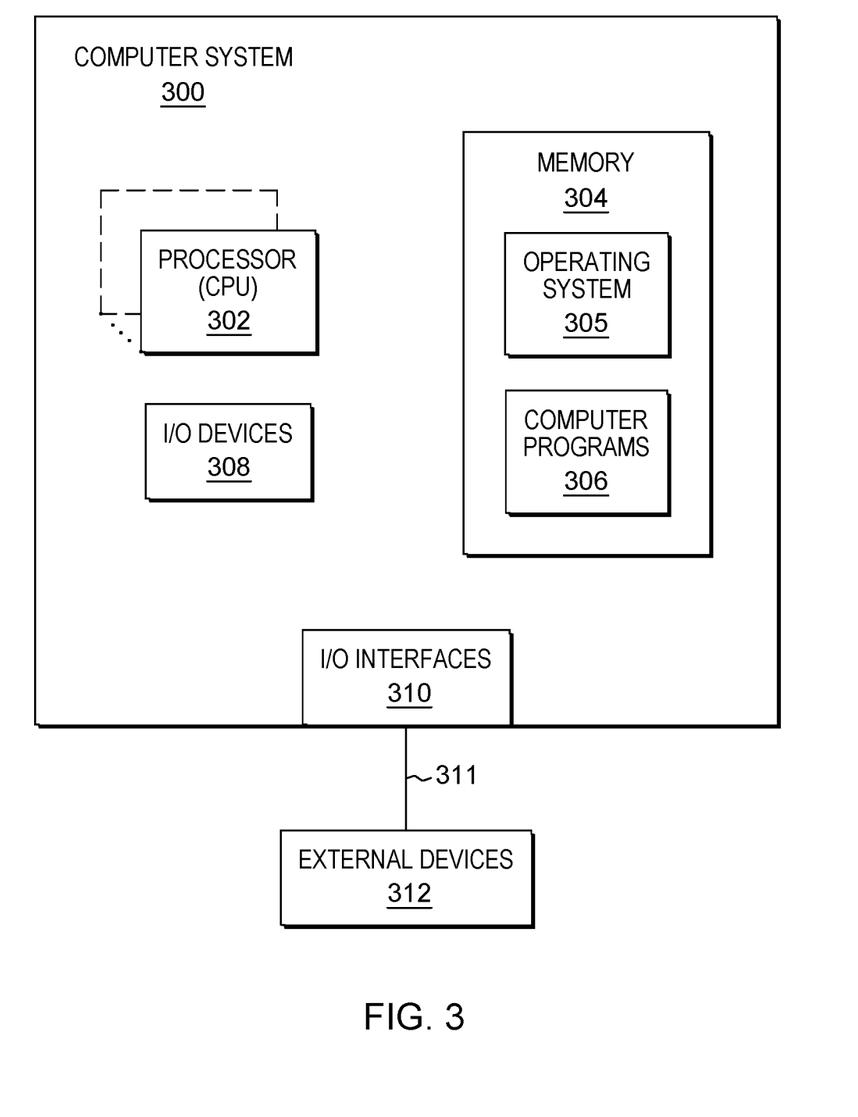
FIG. 3 depicts one example of a computer system and associated devices to incorporate and/or use aspects described herein.

Processes described herein may be performed singly or collectively by one or more computer systems, such as one or more computer systems of or in communication with a vehicle, as an example. FIG. 3 depicts one example of such a computer system and associated devices to incorporate and/or use aspects described herein. A computer system may also be referred to herein as a data processing device/system, computing device/system/node, or simply a computer. The computer system may be based on one or more of various system architectures and/or instruction set architectures, such as those offered by International Business Machines Corporation (Armonk, N.Y., USA), Intel Corporation (Santa Clara, Calif., USA) or ARM Holdings plc (Cambridge, England, United Kingdom), as examples.

FIG. 3 shows a computer system 300 in communication with external device(s) 312. Computer system 300 includes one or more processor(s) 302, for instance central processing unit(s) (CPUs). A processor can include functional components used in the execution of instructions, such as functional components to fetch program instructions from locations such as cache or main memory, decode program instructions, and execute program instructions, access memory for instruction execution, and write results of the executed instructions. A processor 302 can also include register(s) to be used by one or more of the functional components. Computer system 300 also includes memory 304, input/output (I/O) devices 308, and I/O interfaces 310, which may be coupled to processor(s) 302 and each other via one or more buses and/or other connections. Bus connections represent one or more of any of several types of bus structures, including a memory bus or memory controller, a peripheral bus, an accelerated graphics port, and a processor or local bus using any of a variety of bus architectures. By way of example, and not limitation, such architectures include the Industry Standard Architecture (ISA), the Micro Channel Architecture (MCA), the Enhanced ISA (EISA), the Video Electronics Standards Association (VESA) local bus, and the Peripheral Component Interconnect (PCI).

Memory 304 can be or include main or system memory (e.g. Random Access Memory) used in the execution of program instructions, storage device(s) such as hard drive(s), flash media, or optical media as examples, and/or cache memory, as examples. Memory 304 can include, for instance, a cache, such as a shared cache, which may be coupled to local caches (examples include L1 cache, L2 cache, etc.) of processor(s) 302. Additionally, memory 304 may be or include at least one computer program product having a set (e.g., at least one) of program modules, instructions, code or the like that is/are configured to carry out functions of embodiments described herein when executed by one or more processors.

Memory 304 can store an operating system 305 and other computer programs 306, such as one or more computer programs/applications that execute to perform aspects described herein. Specifically, programs/applications can include computer readable program instructions that may be configured to carry out functions of embodiments of aspects described herein.

Examples of I/O devices 308 include but are not limited to microphones, speakers, Global Positioning System (GPS) devices, cameras, lights, accelerometers, gyroscopes, magnetometers, sensor devices configured to sense light, proximity, heart rate, body and/or ambient temperature, blood pressure, and/or skin resistance, and activity monitors. An I/O device may be incorporated into the computer system as shown, though in some embodiments an I/O device may be regarded as an external device (312) coupled to the computer system through one or more I/O interfaces 310.

Computer system 300 may communicate with one or more external devices 312 via one or more I/O interfaces 310. Example external devices include a keyboard, a pointing device, a display, and/or any other devices that enable a user to interact with computer system 300. Other example external devices include any device that enables computer system 300 to communicate with one or more other computing systems or peripheral devices such as a printer. A network interface/adapter is an example I/O interface that enables computer system 300 to communicate with one or more networks, such as a local area network (LAN), a general wide area network (WAN), and/or a public network (e.g., the Internet), providing communication with other computing devices or systems, storage devices, or the like. Ethernet-based (such as Wi-Fi) interfaces and Bluetooth® adapters are just examples of the currently available types of network adapters used in computer systems (BLUETOOTH is a registered trademark of Bluetooth SIG, Inc., Kirkland, Wash., U.S.A.).

The communication between I/O interfaces 310 and external devices 312 can occur across wired and/or wireless communications link(s) 311, such as Ethernet-based wired or wireless connections. Example wireless connections include cellular, Wi-Fi, Bluetooth®, proximity-based, near-field, or other types of wireless connections. More generally, communications link(s) 311 may be any appropriate wireless and/or wired communication link(s) for communicating data.

Particular external device(s) 312 may include one or more data storage devices, which may store one or more programs, one or more computer readable program instructions, and/or data, etc. Computer system 300 may include and/or be coupled to and in communication with (e.g. as an external device of the computer system) removable/non-removable, volatile/non-volatile computer system storage media. For example, it may include and/or be coupled to a non-removable, non-volatile magnetic media (typically called a "hard drive"), a magnetic disk drive for reading from and writing to a removable, non-volatile magnetic disk (e.g., a "floppy disk"), and/or an optical disk drive for reading from or writing to a removable, non-volatile optical disk, such as a CD-ROM, DVD-ROM or other optical media.

Computer system 300 may be operational with numerous other general purpose or special purpose computing system environments or configurations. Computer system 300 may take any of various forms, well-known examples of which include, but are not limited to, personal computer (PC) system(s), server computer system(s), such as messaging server(s), thin client(s), thick client(s), workstation(s), laptop(s), handheld device(s), mobile device(s)/computer(s) such as smartphone(s), tablet(s), and wearable device(s), multiprocessor system(s), microprocessor-based system(s), telephony device(s), network appliance(s) (such as edge appliance(s)), virtualization device(s), storage controller(s), set top box(es), programmable consumer electronic(s), network PC(s), minicomputer system(s), mainframe computer system(s), and distributed cloud computing environment(s) that include any of the above systems or devices, and the like.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
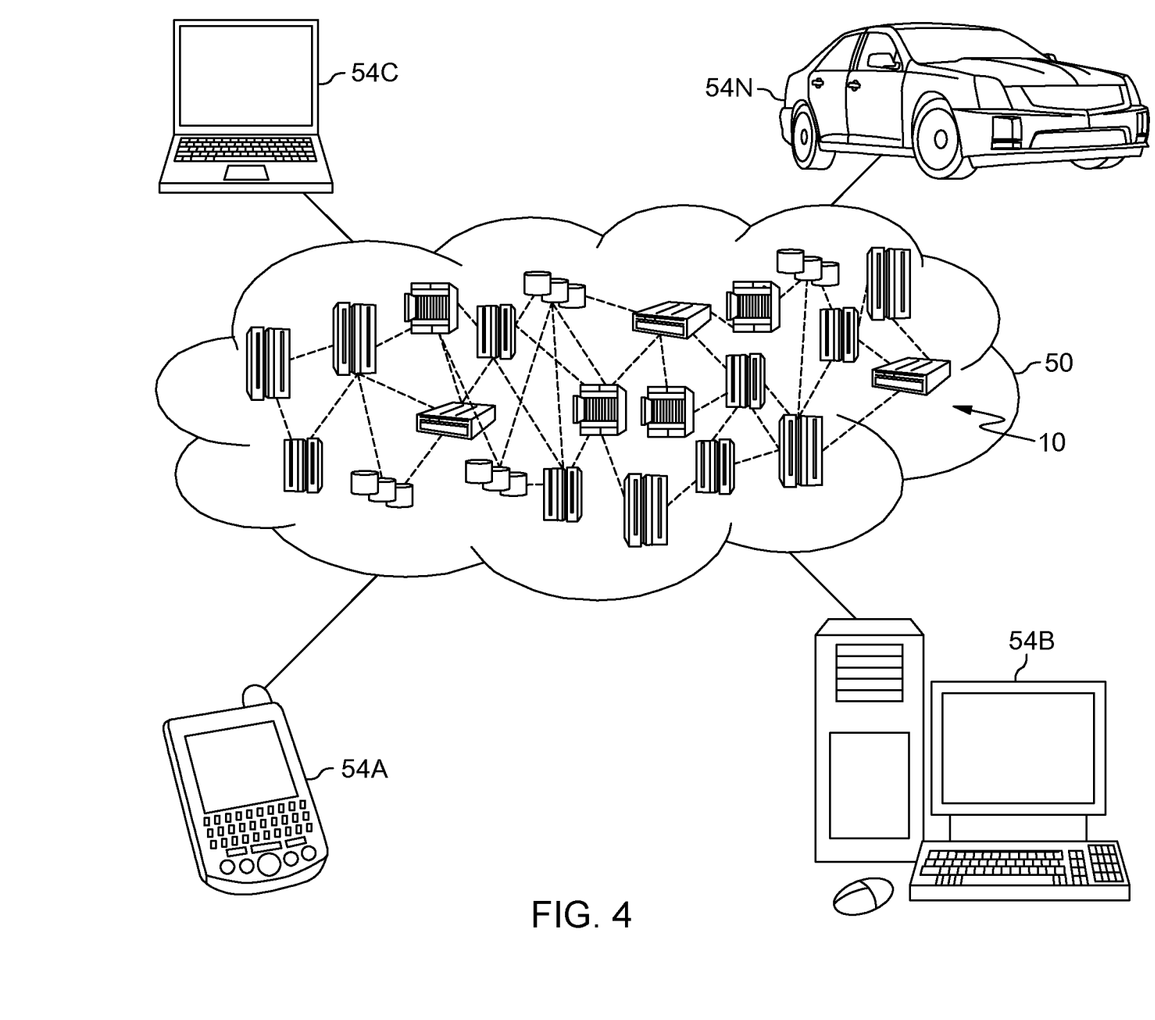
FIG. 4 depicts a cloud computing environment according to an embodiment of the present invention.

Referring now to FIG. 4, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Figure 5:
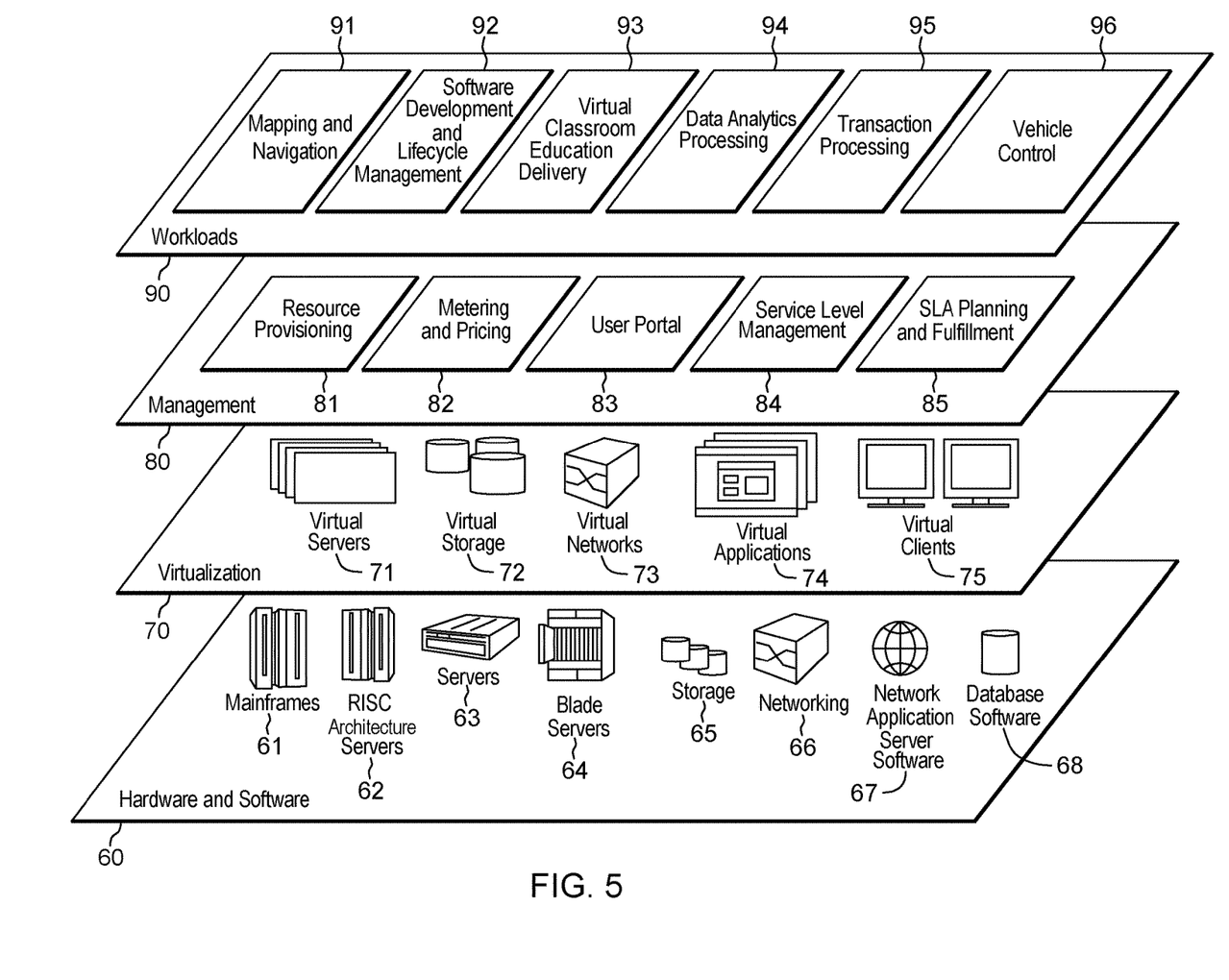
FIG. 5 depicts abstraction model layers according to an embodiment of the present invention.

Referring now to FIG. 5, a set of functional abstraction layers provided by cloud computing environment 50 (FIG. 4) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and vehicle control 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In addition to the above, one or more aspects may be provided, offered, deployed, managed, serviced, etc. by a service provider who offers management of customer environments. For instance, the service provider can create, maintain, support, etc. computer code and/or a computer infrastructure that performs one or more aspects for one or more customers. In return, the service provider may receive payment from the customer under a subscription and/or fee agreement, as examples. Additionally or alternatively, the service provider may receive payment from the sale of advertising content to one or more third parties.

In one aspect, an application may be deployed for performing one or more embodiments. As one example, the deploying of an application comprises providing computer infrastructure operable to perform one or more embodiments.

As a further aspect, a computing infrastructure may be deployed comprising integrating computer readable code into a computing system, in which the code in combination with the computing system is capable of performing one or more embodiments.

As yet a further aspect, a process for integrating computing infrastructure comprising integrating computer readable code into a computer system may be provided. The computer system comprises a computer readable medium, in which the computer medium comprises one or more embodiments. The code in combination with the computer system is capable of performing one or more embodiments.

Although various embodiments are described above, these are only examples. For example, computing environments of other architectures can be used to incorporate and use one or more embodiments.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more embodiments has been presented for purposes of illustration and description, but is not intended to be exhaustive or limited to in the form disclosed. Many modifications and variations will be apparent to those of ordinary skill in the art. The embodiment was chosen and described in order to best explain various aspects and the practical application, and to enable others of ordinary skill in the art to understand various embodiments with various modifications as are suited to the particular use contemplated.

What is claimed is:

1. A computer-implemented method comprising:
receiving position data of a vehicle, the position data indicating a geolocation of a vehicle traveling in an area;
correlating the received position data to a map including mapped areas designated as non-roadway areas, wherein the correlating determines based on the geolocation of the vehicle that the vehicle is located and traveling entirely in a designated non-roadway area;
after, and based on, determining that the vehicle is located and traveling entirely in the designated non-roadway area, checking one or more restrictions placed on vehicular travel in the non-roadway area in which the vehicle is traveling, wherein a restriction of the one or more restrictions comprises a speed restriction indicating a threshold speed of vehicular travel the non-roadway area; and
based on the one or more restrictions and on checking the one or more restrictions after determining that the vehicle is located and traveling entirely in the designated non-roadway area, performing processing to undertake at least one action, the at least one action comprising automatically initiating an alert to law enforcement based on observing that the vehicle travels in the non-roadway in excess of the threshold speed and controlling at least one function of the vehicle, wherein the controlling the at least one function comprises automatically autonomously driving the vehicle to a law enforcement facility which contains the vehicle and any occupants thereof.

2. The method of claim 1, wherein the controlling at least one function further comprises automatically controlling a speed of the vehicle, the controlling the speed including slowing the vehicle from an initial speed to a slower speed.

3. The method of claim 1, wherein the controlling at least one function further comprises initiating guiding the vehicle back onto the roadway, the roadway being adjacent to the non-roadway area, as part of the automatically autonomously driving the vehicle to the area that securely contains the vehicle and any occupants thereof.

4. The method of claim 1, wherein the at least one action further comprises locating the law enforcement facility based on the map and the geolocation of the vehicle.

5. The method of claim 1, further comprising ascertaining a physical state of the driver, wherein the ascertained physical state indicates a medical emergency.

6. The method of claim 1, wherein the one or more restrictions indicate an exception for designated privileged vehicles, the designated privileged vehicles including law enforcement and emergency vehicles.

7. The method of claim 1, wherein the controlling at least one function of the vehicle further comprises automatically activating audio and visual alert devices of the vehicle.

8. The method of claim 1, wherein the at least one action further comprises automatically sending electronic communications from the vehicle to devices within a threshold distance of the vehicle.

9. The method of claim 1, further comprising determining autonomous capabilities of the vehicle, the determining comprising receiving, from the vehicle, one or more communications of metadata maintained by the vehicle and informing of:
whether, and to what extent, the vehicle can autonomously drive itself;
whether the vehicle possesses automatic steering capability;
whether speed of the vehicle can be controlled by the vehicle without driver intervention;
whether the vehicle reads map data; and
whether the vehicle possesses lane detection capability.

10. A computer system comprising:
a memory; and
a processor in communication with the memory, wherein the computer system is configured to perform a method comprising:
receiving position data of a vehicle, the position data indicating a geolocation of a vehicle traveling in an area;
correlating the received position data to a map including mapped areas designated as non-roadway areas, wherein the correlating determines based on the geolocation of the vehicle that the vehicle is located and traveling entirely in a designated non-roadway area;
after, and based on, determining that the vehicle is located and traveling entirely in the designated non-roadway area, checking one or more restrictions placed on vehicular travel in the non-roadway area in which the vehicle is traveling, wherein a restriction of the one or more restrictions comprises a speed restriction indication a threshold speed of vehicular travel the non-roadway area; and
based on the one or more restrictions and on checking the one or more restrictions after determining that the vehicle is located and traveling entirely in the designated non-roadway area, performing processing to undertake at least one action, the at least one action comprising automatically initiating an alert to law enforcement based on observing that the vehicle travels in the non-roadway in excess of the threshold speed and controlling at least one function of the vehicle, wherein the controlling the at least one function comprises automatically autonomously driving the vehicle to a law enforcement facility which contains the vehicle and any occupants thereof.

11. The computer system of claim 10, wherein the controlling at least one function further comprises automatically controlling a speed of the vehicle, the controlling the speed including slowing the vehicle from an initial speed to a slower speed.

12. The computer system of claim 10, wherein the method further comprises ascertaining a physical state of the driver, wherein the ascertained physical state indicates a medical emergency.

13. The computer system of claim 10, wherein the one or more restrictions indicate an exception for designated privileged vehicles, the designated privileged vehicles including law enforcement and emergency vehicles.

14. The computer system of claim 10, wherein the method further comprises determining autonomous capabilities of the vehicle, the determining comprising receiving, from the vehicle, one or more communications of metadata maintained by the vehicle and informing of:
- whether, and to what extent, the vehicle can autonomously drive itself;
- whether the vehicle possesses automatic steering capability;
- whether speed of the vehicle can be controlled by the vehicle without driver intervention;
- whether the vehicle reads map data; and
- whether the vehicle possesses lane detection capability.

15. A computer program product comprising:
a computer readable storage medium readable by a processing circuit and storing instructions for execution by the processing circuit for performing a method comprising:
  receiving position data of a vehicle, the position data indicating a geolocation of a vehicle traveling in an area;
  correlating the received position data to a map including mapped areas designated as non-roadway areas, wherein the correlating determines based on the geolocation of the vehicle that the vehicle is located and traveling entirely in a designated non-roadway area;
  after, and based on, determining that the vehicle is located and traveling entirely in the designated non-roadway area, checking one or more restrictions placed on vehicular travel in the non-roadway area in which the vehicle is traveling, wherein a restriction of the one or more restrictions comprises a speed restriction indicating a threshold speed of vehicular travel the non-roadway area; and
  based on the one or more restrictions and on checking the one or more restrictions after determining that the vehicle is located and traveling entirely in the designated non-roadway area, performing processing to undertake at least one action, the at least one action comprising automatically initiating an alert to law enforcement based on observing that the vehicle travels in the non-roadway in excess of the threshold speed and controlling at least one function of the vehicle, wherein the controlling the at least one function comprises automatically autonomously driving the vehicle to a law enforcement facility which contains the vehicle and any occupants thereof.

16. The computer program product of claim 15, wherein the controlling at least one function further comprises automatically controlling a speed of the vehicle, the controlling the speed including slowing the vehicle from an initial speed to a slower speed.

17. The computer program product of claim 15, wherein the method further comprises ascertaining a physical state of the driver, wherein the ascertained physical state indicates a medical emergency.

18. The computer program product of claim 15, wherein the one or more restrictions indicate an exception for designated privileged vehicles, the designated privileged vehicles including law enforcement and emergency.

\* \* \* \* \*